US012485260B2

(12) United States Patent

Jorgensen de Vizacarrondo et al.

(10) Patent No.: US 12,485,260 B2

(45) Date of Patent: Dec. 2, 2025

(54) WEARABLE DEVICE FOR TRANSDERMAL PRODUCT SUPPLY

(71) Applicants: Medicsensors Limited, Leeds (GB); Agencia Estatal Consejo Superior de Investigaciones Cientificas, M.P., Madrid (ES)

(72) Inventors: Eduardo Walther Jorgensen de Vizacarrondo, Madrid (ES); Jose Carlos Montesinos Perez, Madrid (ES); Juan Cesar de Mercado Santamarta, Madrid (ES); Francisco Ramon Montero de Espinosa Freijo, Madrid (ES)

(73) Assignees: Medicsensors Limited, Leeds (GB); Agencia Estatal Consejo Superior de Investigaciones Cientificas, M.P., Madrid (ES)

(*) Notice: Subject to any disclaimer, the term of this patent is extended or adjusted under 35 U.S.C. 154(b) by 658 days.

(21) Appl. No.: 17/998,474

(22) PCT Filed: Apr. 12, 2021

(86) PCT No.: PCT/ES2021/070237

§ 371 (c)(1),
(2) Date: Nov. 10, 2022

(87) PCT Pub. No.: WO2021/229117

PCT Pub. Date: Nov. 18, 2021

(65) Prior Publication Data

US 2023/0241365 A1 Aug. 3, 2023

(30) Foreign Application Priority Data

May 12, 2020 (EP) .................................... 20382391

(51) Int. Cl.
*A61M 37/00* (2006.01)

(52) U.S. Cl.
CPC .............................. *A61M 37/0092* (2013.01)

(58) Field of Classification Search
CPC ...... A61M 37/0092; A61M 2037/0007; A61M 2205/3375; A61B 2090/378;
(Continued)

(56) References Cited

U.S. PATENT DOCUMENTS 5,421,816 A * 6/1995 Lipkovker ........ A61M 37/0092 604/20
5,655,539 A 8/1997 Wang et al.
(Continued)

OTHER PUBLICATIONS

European Patent Office, International Search Report, mailed Aug. 23, 2021, in International Patent Application No. PCT/ES2021/070237, filed Apr. 12, 2021.
(Continued)

*Primary Examiner* — Jason E Flick

(74) *Attorney, Agent, or Firm* — Thedford I. Hitaffer; Hitaffer, PLLC

(57) ABSTRACT

A wearable device for transdermal product supply comprises a head, which houses two ultrasonic resonators in resonance, with an outer cavity. A first, more distal resonator emits towards the skin at a first frequency and a second, more proximal resonator surrounds the cavity and emits parallel to the skin at a second frequency. One frequency is high-frequency sonophoresis (HFS) and the other is low-frequency sonophoresis (LFS). The second resonator comprises a hole in order to enable the waves from the first resonator to pass through. The waves from the second resonator pass through the head, the hole and the cavity, bouncing off an opposite area of the head and interfering with the waves from the first resonator. The interference between the waves creates a stationary field which increases the permeability of the skin, enabling a device with a reduced size to be incorporated into a wearable.

15 Claims, 5 Drawing Sheets

(58) Field of Classification Search
CPC ...... A61B 8/4281; A61B 8/4272; A61N 7/00; A61N 2007/0004; A61N 2007/0056; A61N 2007/0073; A61N 2007/0078
See application file for complete search history.

(56) References Cited

U.S. PATENT DOCUMENTS 6,491,657 B2 * 12/2002 Rowe ............... A61B 5/150099
604/22
2016/0015954 A1 * 1/2016 Slayton ............. A61M 37/0092
604/22

OTHER PUBLICATIONS

European Patent Office, Written Opinion, mailed Aug. 23, 2021, in International Patent Application No. PCT/ES2021/070237, filed Apr. 12, 2021.

* cited by examiner

WEARABLE DEVICE FOR TRANSDERMAL PRODUCT SUPPLY

CROSS-REFERENCE TO RELATED APPLICATIONS

This application, filed under 35 USC 371, is a United States National Stage Application of International Application No. PCT/ES2021/070237, filed Apr. 12, 2021, which claims priority to EP Application Serial No. 20382391.9, filed on May 12, 2020, the disclosures of which are incorporated herein by reference in their entirety.

DESCRIPTION

Technical Field of the Invention

The present invention can be included within the health and personal care sector, more specifically for supplying products with active substances, such as, for example, drugs and cosmetics. More particularly, the object of the invention is a wearable device for supplying products transdermally and non-invasively.

Background of the Invention

There are different techniques and devices for transdermally and non-invasively supplying drugs, the molecule of which has a considerable size, such as insulin.

To do so, it is necessary for the drug to pass through the stratum corneum of the skin of the patient, which has a low absorption capacity, especially for molecules with a high molecular weight, such as insulin.

The structure of human skin has a stratum corneum, which consists of an external layer of dead cells (corneocytes) embedded in a lipid matrix, which makes it difficult for substances to diffuse through said stratum corneum, especially substances, such as insulin, with a molecular size greater than that of the pores of the skin.

In this sense, several techniques were initially developed, such as electrophoresis (with voltages up to 150 V) or iontophoresis, with lower voltages.

Beginning in 1950, the benefits of sonophoresis were discovered, which consists of applying ultrasound on a fluid, which is in contact with the skin, and which contains the substance to be applied to the interior of the skin. Initially, frequencies from 700 KHz to 10000 kHz (high-frequency sonophoresis, HFS) were used to transfer corticosteroids, with transfers up to ten times greater than without the application of ultrasound, thanks to the effect of stable cavitation, with bubbles oscillating within the stratum corneum in the lipid matrix, disorganizing the layers of the stratum corneum in order to enable better permeability of small molecules.

Beginning in the 1990s, knowing that cavitation improves the transfer of certain substances through the skin when applying ultrasound, and that the effects associated with cavitation in liquids increase inversely with the frequency, studies on sonoporation at medium and low frequency were started. The effect with low frequencies 20-100 kHz (low-frequency sonophoresis, LFS) began to be studied, discovering that in LFS, the lower the frequency, the greater the permeability, which demonstrates that transient cavitation is the most important mechanism for improving the permeability of the skin with LFS.

Since 1996, several studies have been published regarding multifrequency sonophoresis—one frequency in the HFS range and another frequency in the LFS range—with satisfactory results with respect to the application of HFS and LFS separately. However, there is the drawback that, for the application of the LFS frequency, the size of the transducer used to provide the LFS frequency wave increases the lower the frequency and the greater the intensity, therefore, the size of the device which provides intensities that are high enough turns out to be too high to be part of a wearable. In other words, the low-frequency ultrasonic transducers used to achieve the necessary intensities are too large to be able to be added to a wearable device.

SUMMARIZED DESCRIPTION OF THE INVENTION

The present invention describes a device for supplying products transdermally, in a non-invasive manner and which is wearable, thanks to a combination of two ultrasonic resonators, for example, of a piezoelectric kind, housed in one same head, one in a distal position and another in a proximal position, such that each resonator, in combination with the configuration of the head, defines a transducer, wherein one of the resonators works in resonance at an LFS frequency and the other works in resonance at an HFS frequency, likewise the resonator located in the proximal position has an inner through hole which is passed through by the emission from the other more distal resonator, such that the emissions from both resonators interact creating a stationary field which increases the permeability effects for a given resonator size, such that it enables the size of the device to be reduced in order to obtain a predetermined performance.

By means of the device of the invention, the product passes through the stratum corneum by means of cavitation and opening pores, in a reversible manner and without causing damage to the skin.

The device of the invention optionally has a medical use, although not in an exclusive manner, as will be explained later.

Normally, according to the state of the prior art, the thickness and magnitude of the resonators is defined by the frequency and the intensity at which they are to work. However, the device of the invention manages to amplify the resulting waves, obtaining resonance peaks at the desired frequencies, particularly in the scope of the LFS frequency, due to the fact that the design thereof emits the wavefronts in different manners throughout the entire structure of the head thereof, providing as a result a resulting wave at the desired frequency and intensity, both in the case of LFS, as well as in the case of HFS, creating a stationary field which amplifies the effect of the permeability, as mentioned previously. All this enables the device to be built within a size suitable to make up part of a wearable.

The configuration of the device enables it to be applied in order to supply various products. The products can be liquids with a higher or lower density or viscosity, likewise they can have a non-liquid texture, such as gels, ointments or creams. The device may be a device for medical use, since the products, both the liquid ones and those with a non-liquid texture, may contain drugs, such as insulin. Alternatively, the device can be configured to supply other types of products, such as cosmetic products, which can also be liquids or have a non-liquid texture, for example, creams, gels, ointments, etc. as mentioned above.

The invention has a preferred exemplary embodiment wherein the resonator located in the proximal position works in resonance at the LFS frequency and the resonator located in the distal position works in resonance at the HFS frequency, and another preferred exemplary embodiment wherein the opposite occurs, i.e. the resonator located in the proximal position works in resonance at the HFS frequency and the resonator located in the distal position works in resonance at the LFS frequency.

BRIEF DESCRIPTION OF THE FIGURES

The foregoing and other advantages and features will be better understood based on the following detailed description of several embodiments in reference to the attached drawings, which must be interpreted in an illustrative and non-limiting manner and in which:

FIGS. 2A and 2B, FIG. 2A shows a schematic cross-sectional side view of the configuration of a first exemplary embodiment of the device of the invention, while FIG. 2B shows a cross-sectional side view of the head.

FIGS. 3A and 3B, FIG. 3A shows a schematic cross-sectional side view of the configuration of a second exemplary embodiment of the device of the invention, while FIG. 3B shows a cross-sectional side view of the head.

DETAILED DESCRIPTION OF A PREFERRED EMBODIMENT OF THE INVENTION

Next, with help from aforementioned FIGS. 1-3B, a detailed description is offered of a preferred exemplary embodiment of a wearable medical device for transdermally supplying products in general and that, in a particular but not exclusive manner, is intended for supplying drugs, more specifically, insulin, and which enables the product to pass through the stratum corneum of the skin of the user by means of cavitation and opening the pores, in a reversible manner and without causing damage to the skin.

Figure 1:
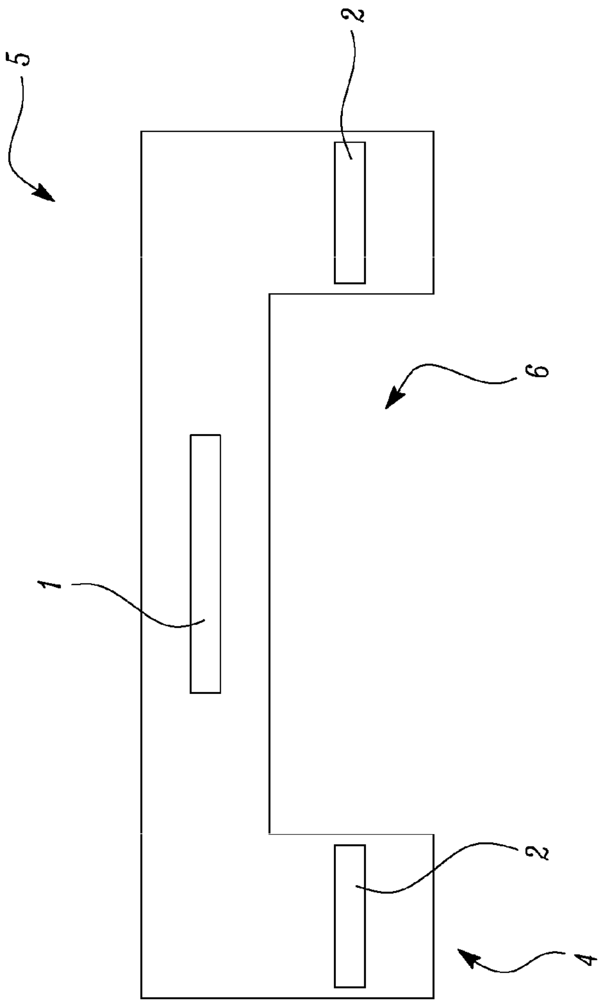
FIG. 1 shows a schematic side view of the head of the device.

As illustrated by means of FIG. 1, the device of the invention comprises two ultrasonic resonators (1, 2), for example, of a piezoelectric kind, housed within one same head (3). The head (3) has a proximal area (4) intended to be in contact with the skin of the user, as well as a distal area (5), opposite from the proximal area (4) and, therefore, farther away from the skin of the user.

In the proximal area (4), the head (3) has an outer cavity (6) intended to house, when used, an ultrasound conductive substance, which can be liquid or can have a non-liquid texture, such as ointment, cream or gel, in order to prevent the presence of gas and, therefore, enable the transfer of the ultrasonic waves from the head (3) to the skin. Generally, the ultrasound conductive substance coincides with the very product to be applied, although it does not necessarily have to be this way. In particular, the product can be deposited on the head (3) inside the cavity (6), and then the head (3) is applied against the skin in order to bring the skin into contact with the product. Alternatively, the device may be applied on reservoirs of product (not shown), such as patches, which are arranged as fastened (e.g. by adhesive), or only superimposed on the skin of the user. Another possibility, by way of illustration, is that the device additionally includes supply elements (not shown) which are attachable, either detachably or not detachably, to the head (3) in the vicinity of the cavity (6) in order to enable the product to be supplied, in particular, according to predetermined doses. The head (3) is preferably made of biocompatible material or materials.

The resonators (1, 2) comprise a first resonator (1), located in the distal area (5) and, therefore, unaffected by the cavity (6), as well as a second resonator (2), in the proximal area (4), which surrounds at least part of the cavity (6), as explained below. The resonators (1, 2) are intended to emit narrow band ultrasonic waves and to work in resonance, each resonator (1,2) at a predetermined frequency.

The first resonator (1), which may for example be shaped like a disc, emits, when used, ultrasonic radiation towards the skin of the user, generally in a direction perpendicular to said skin which is oriented towards the cavity (6), at a first frequency. Moreover, the second resonator (2), which emits, when used, waves at a second frequency, is hollow, i.e. it comprises an inner through hole (7) in order to enable the waves of the first frequency to pass through without hitting the second resonator (2). Preferably, the inner through hole (7) is larger than the first resonator (1), so that all the waves emitted by the first resonator (1) pass through the hole (7) of the second resonator (2). The second resonator (2) can have the shape of a toroid, whether it has a generatrix that is circular, square, etc., as well as a directrix that is circular or another type. Preferably, it has the shape of a circular torus, i.e. a ring torus, or a toroid with a rectangular cross section.

The first resonator (1) is located superimposed over the second resonator (2), but not housed in said second resonator (2), i.e. it is at a different height. The superimposition enables the waves emitted by the first resonator (1) to not collide with the second resonator (2), but rather to pass through the hole (7), as indicated previously.

A portion of the cavity (6) of the head (3), corresponding to the height of the second resonator (2), is surrounded by said second resonator (2). Consequently, the waves emitted by the second resonator (2) are essentially parallel to the skin, and enable the permeabilizing effect of the actions of the first resonator (1) to be amplified.

The head (3) has a triple function of supporting the resonators (1, 2), providing physical continuity for the path of the waves, and causing resonance at the first and second frequencies, as explained below. The head (3) is preferably made of metal, such as aluminium, or alternatively, biocompatible polymeric material, such as polypropylene. Preferably, the head (3) is a monobloc body. The resonators (1, 2) are assembled on the head (3), which is configured such that, once the resonators (1, 2) have been assembled, the waves emitted by the resonators (1, 2) circulate through the head (3) without encountering gaseous matter before leaving the head (3), in order to prevent a malfunction of the resonators (1, 2). By way of example, as illustrated in FIGS. 2A, 2B, 3A and 3B, the head (3) comprises a housed portion (13), which is housed in the hole (7) of the second resonator (2), preferably occupying a peripheral portion of the hole (7). Preferably, the housed portion (13) makes up an integral part of the head (3).

As mentioned before, the second resonator (2) has a hole (7), for example, because it is equipped with the aforementioned ring shape, and is housed inside the head (3) in correspondence with the cavity (6), such that the cavity (6) also occupies the hole (7), together with the housed portion (13) of the head (3). Consequently, and first of all, the radiation emitted by the first resonator (1) towards the skin of the user passes through the hole (7) and the cavity (6) and reaches the skin. Second of all, the waves generated by the second resonator (2), horizontally, do not escape from the head (3) out to "infinity", but are emitted through the hole (7), thereby travelling through the head (3) and the cavity (6), for which reason they collide, bouncing off an opposite area of the head (3) itself and, since they are generated in all horizontal directions, a stationary field is created in the cavity (6) for the waves from the second resonator (2), which interacts with that of the first resonator (1), which, under resonance conditions, increases the effect exerted on the skin in the area surrounded by the head (3) and the second resonator (2), further increasing the permeability in the area of the affected skin and, therefore, the effectiveness of the supply. Therefore, it is possible to obtain the desired resonance and intensity conditions in a device with such a small size so as to be incorporated into a wearable.

The frequency at which one of the two resonators (1, 2) emits, the first (1) or the second (2), is a frequency significantly lower than the frequency at which the other resonators emit (1, 2), which is higher. The low frequency is in the typical LFS zone, i.e. the lowest ultrasonic zone, between approximately 20 KHz and 100 KHz. Values closer to 20 KHz, at the upper threshold of human hearing, produce satisfactory results, although at the cost of generating auditory discomfort in users. A frequency within a 55 kHz environment, between 50 KHz and 60 KHz, has been chosen as the preferred low frequency. Moreover, the high frequency is in the typical HFS zone, for example, around 1 MHZ, between 800 kHz and 1200 kHz. The invention works satisfactorily if the first frequency is the high frequency and the second frequency is the low frequency, or in the opposite case.

Another feature of the device of the invention, apart from the configuration of the resonators (1, 2) and the assembly thereof in the head (3), indicated above, is the handling of the resonance, as explained below.

As previously indicated, one of the resonators (1, 2) is intended to be supplied at an HSF frequency, in order to emit ultrasound at the HSF frequency, and to resonate at the HSF frequency, while the other resonator (1,2) is intended to be supplied at an LSF frequency, in order to emit ultrasound at the LSF frequency and to resonate at the LSF frequency. Each of the resonators (1, 2) possesses, due to how it is constructed, its fundamental frequency of vibration according to certain vibration mode(s), for example, in thickness mode or in radial mode.

For example, solid resonators (1, 2) in the shape of a cylinder (disc) have a fundamental frequency in thickness mode which decreases as the resonator size is increased and vice versa. For example, a 4 MHz ceramic can have a thickness of 0.5 mm and a diameter of 6 mm, while a 2 MHz ceramic can have a thickness of 1 mm and a diameter of 6 mm, and a 1 MHz ceramic can have a thickness of 2 mm and a diameter of 10 mm. In other words, a resonator (1, 2) in the shape of a disc with a reduced size, like the first resonator (1), is suitable for obtaining a resonance at HFS frequency in thickness mode without needing adaptations.

However, a hollow resonator (1, 2), for example in the shape of a toroid, such as the second resonator (2) must have a large size, which is unacceptable in a wearable device, in order to work in thickness mode resonance at an LFS frequency.

In order to solve the aforementioned drawback, the present invention presents two types of solutions, indicated below, and which are described in detail later in the examples.

A first solution consists of using a first resonator (1), which is solid, for example in the shape of a disc, equipped with a fundamental frequency in thickness mode within the HFS range, in order to work, as explained below, in resonance at LFS frequency, including in the head (3) some component (8, 9, 10) intended to be in contact with the first resonator (1), such that an assembly of first resonator (1)+head (3) is formed, with physical continuity, constituting a transducer which resonates in flextensional mode at LFS frequency when supplied at LFS frequency, even though the LFS frequency is not a fundamental frequency in thickness mode of the first resonator (1). The second resonator (2), with a hollow shape, such as a ring, can have a fundamental frequency in thickness mode within the HFS range, such that it will resonate at HFS frequency when supplied with HFS frequency. The first example, which will be described in detail below, according to FIGS. 2A and 2B, indicates dimensions and features that support what was explained in the first solution.

Moreover, the second solution consists of taking advantage of the fact that the second resonator (2), with a hollow shape, such as a ring, has, due to the size and construction thereof, a fundamental frequency, not in thickness mode, but in radial mode, within the LFS range. Therefore, the second resonator (2) will work in resonance in radial mode at LFS frequency when it is supplied with LFS frequency. Moreover, the first resonator (1), in the shape of a disc, due to the dimensions thereof, will have a fundamental frequency in thickness mode within the HFS range, with which it will resonate at HFS frequency when supplied with HFS frequency. The second example, which will be described in detail below, according to FIGS. 3A and 3B, indicates dimensions and features that support what was explained in the second solution.

DESCRIPTION OF THE EXAMPLES

Figure 2A:
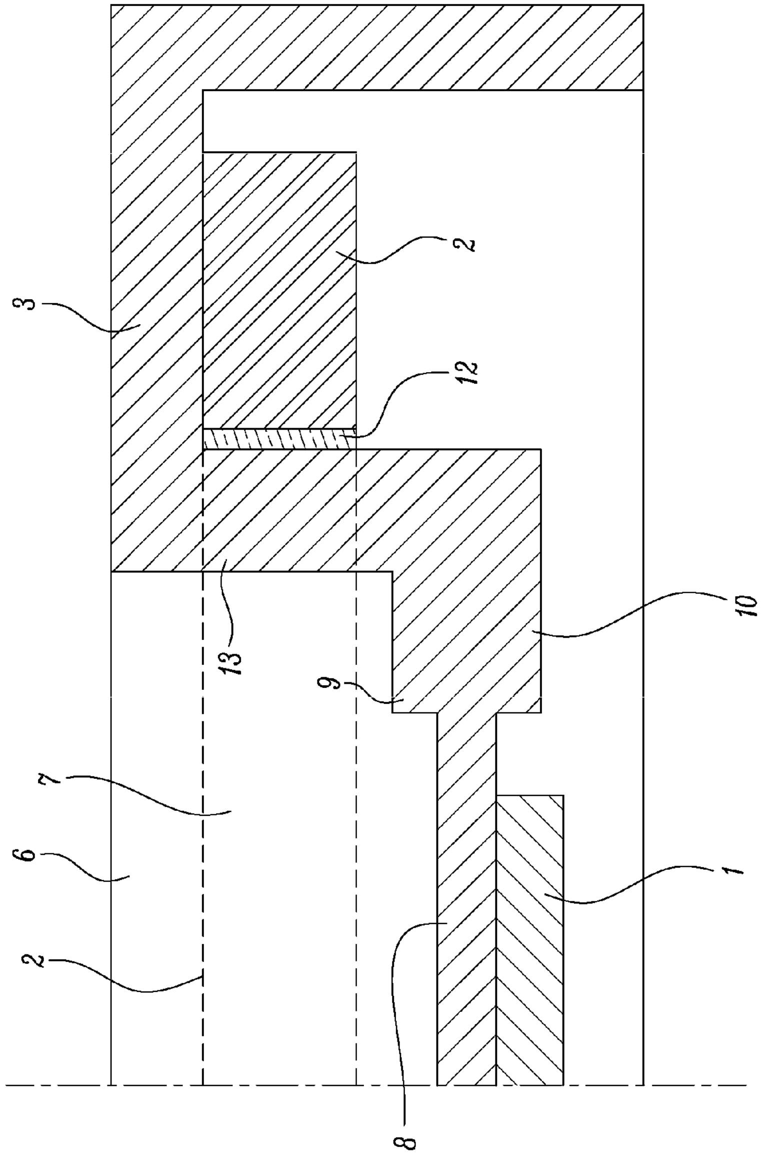
Figure 2B:
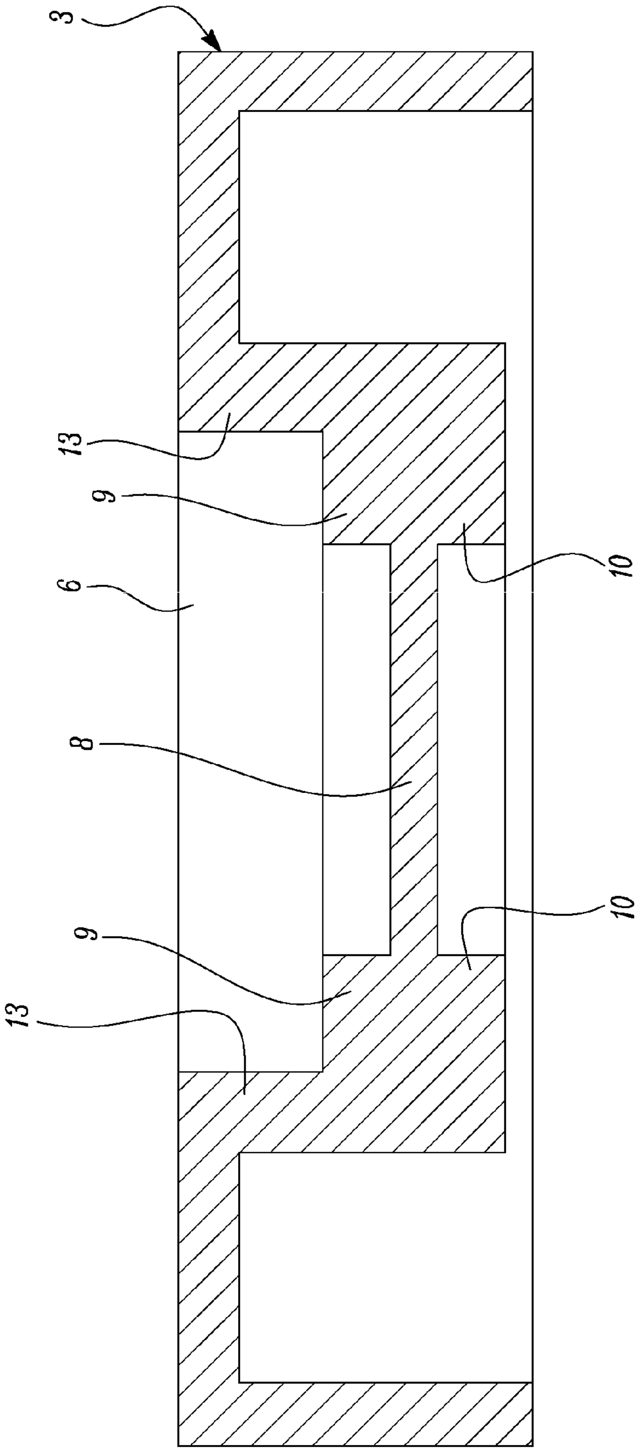
Figure 3A:
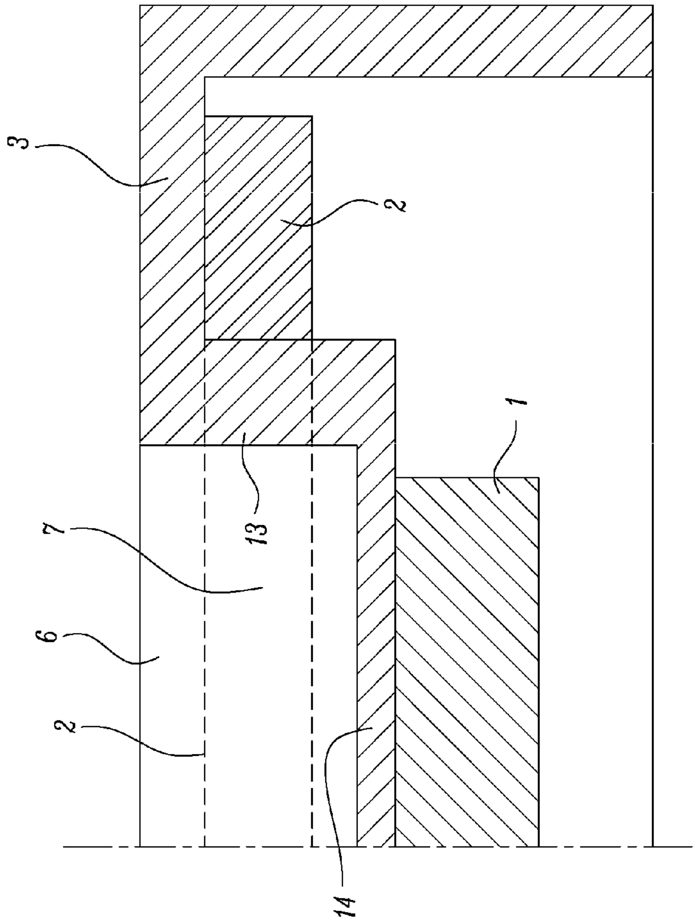
Figure 3B:
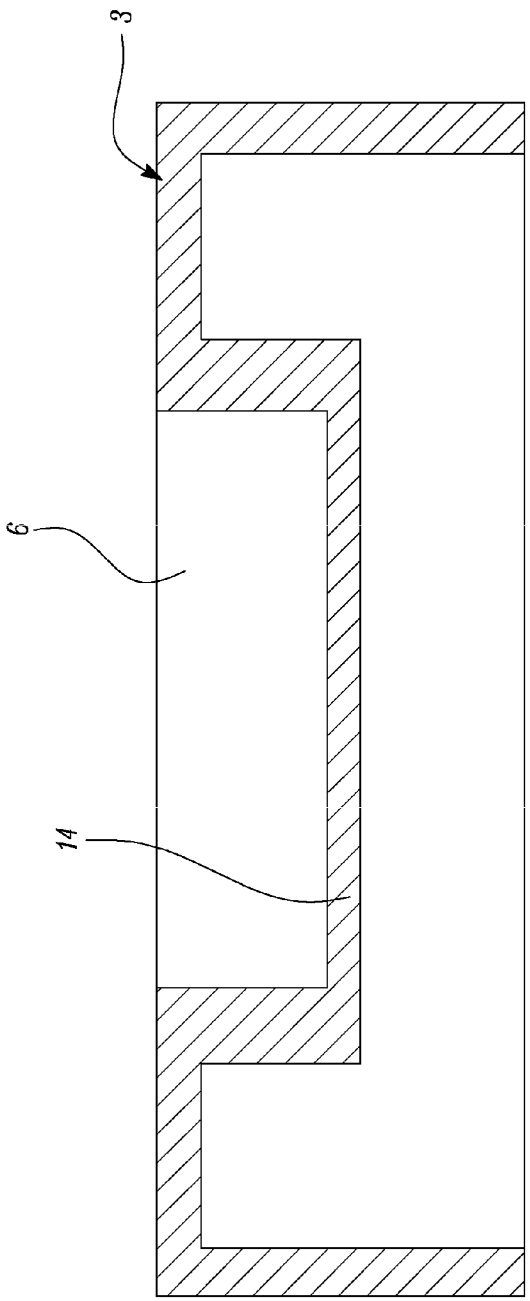

The device of the invention has an operation that can be based on different types of operation of the resonators (1, 2), such as flexion-transmission (see FIGS. 2A and 2B) and transmission-transmission (see FIGS. 3A and 3B). For resonators (1, 2) that operate in flexion-transmission, according to FIGS. 2A and 2B, a membrane (8), preferably made of metal, is arranged generally as an integral portion of the head (3), and which is vibrating by flexion, in contact with the first resonator (1). Moreover, the head (3) can further include two projections (9, 10), one proximal (9) and another distal (10), wherein the projections (9, 10) cooperate with the membrane (8) in order to work in resonance, together with the first resonator (1), in flextensional mode at a predetermined LFS frequency. In the case of transmission-transmission, according to FIGS. 3A and 3B, the membrane (8) is not required, although similarly, the head (3) can include a transmission disc (14) for transmitting vibration.

The height of the cavity (6) is related to the height of the second resonator (2), which will be approximately 1-2 mm, according to a preferred exemplary embodiment, and which has been chosen based on the content of the desired product which is to be able to be housed inside the cavity (6), since a reduced amount would require the user to have to replace product in the cavity (6) often, as well as a high amount would cause a greater risk of administering a greater amount. The cavity (6) contains, when used, an ultrasound conductive substance, in order to prevent the presence of gas and, therefore, enable the transfer of the ultrasonic waves from the head (3) to the skin. The ultrasound conductive substance may be a liquid or it may have a non-liquid texture, such as cream, gel, ointment, etc., provided it is ultrasound conductive. In particular, it can be the very product to be applied, when it is ultrasound conductive. The device of the invention can also be used to supply products with a non-liquid texture, such as the aforementioned creams, gels, ointments, etc. To do so, first of all, the device of the invention is used with the ultrasound conductive substance, which can be harmless, in order to generate the effects of cavitation and opening the pores in the skin and, subsequently, these effects are taken advantage of in order to, without using the device, apply and absorb an active product with a non-liquid texture, such as cream, gel, ointment, etc.

By way of illustrative, non-limiting example, the head (3) has a cylindrical shape with an upside-down U-shaped cross section, with a diameter of about 25 mm and a height of about 2-10 mm, preferably 5-10 mm, with the cavity (6) having a height of approximately 2-3.3 mm.

Wave emissions that produce high ultrasonic intensities, greater than 0.5 W/cm$^2$, preferably greater than 1 W/cm$^2$, are more convenient in order to achieve sufficiently high acoustic pressures to favor the aforementioned combined effects of generating a sufficient number of cavitation bubbles and opening the pores in the skin by imploding the cavitation bubbles. In this sense, intensities higher than 1 W/cm$^2$ are considered sufficiently suitable. In order to meet limitations imposed by several laws, it is preferable to maintain the intensity values between 1 W/cm$^2$ and 2 W/cm$^2$, in particular, in order to prevent eventual risks of skin damage.

Two illustrative examples of the features of the head (3) with the two resonators (1,2) are shown below, as illustrated in FIGS. 2A, 2B, 3A and 3B.

In both examples, the head (3) is a monobloc body made of aluminium. Alternatively, it could be a monobloc body made of polypropylene.

According to a first example, see FIGS. 2A, 2B, called flexion-transmission, the following components are included:

- First resonator (1), configured as a ceramic disc for power applications, with a variable thickness between 0.5 mm and 1 mm and a diameter of 6 mm, with a fundamental frequency of vibration in thickness of 2 or 4 MHz.
- Second resonator (2), configured in ceramic for power applications, as a toroid with a rectangular cross section and a circular directrix, a thickness of 2 mm, with an external diameter of 20 mm, and an internal diameter of 14 mm, and with a fundamental frequency of vibration in thickness of 1 MHz.
- Vibrating membrane (8) with a diameter of 11 mm and variable thickness, inserted between the first resonator (1) and the second resonator (2), in contact with the first resonator (1), and in order to, together with the first resonator (1), vibrate in flextensional mode supplied by the first resonator (1).
- Cavity (6), with a variable height and a diameter of 11 mm, on the membrane (8).
- Two projections (9, 10), one proximal (9) and the other distal (10), between which the membrane (8) is supported, wherein the distal projection (10) has an external diameter of 14 mm and an internal diameter of 8 mm, while the proximal projection (9) has an external diameter of 11 mm and an internal diameter of 8 mm. The projections (9, 10) cooperate with the membrane (8) in order to work in resonance, together with the first resonator (1), at the predetermined LFS frequency of 55 KHz.
- Head (3), for fixing the resonators (1, 2), made up in part by the membrane (8) and the projections (9, 10), and which is supplied with vibration in transmission by the first resonator (1).
- Housed portion (13) which makes up part of the head (3), and which is intended to be housed in a more peripheral area of the hole (7).
- Adhesive layer (12), with a variable thickness, between the second resonator (2) and the head (3).

In the first example, the coupled "thickness" mode of the second resonator (2) is used, transferring the resonance vibration in direct transmission to the head (3) to which it is adhered, wherein the resonance frequency of the second resonator (2) essentially depends on the shape and material of the second resonator (2), although with slight variations due to the wall thickness of the head (3). Likewise, the first resonator (1) is used as a supplier for a main frequency, with a flexural mode at 55 kHz, which is a function of the features of the first resonator (1), in particular, the overall flexion of the first resonator (1), and of the configuration of the vibrating membrane (8) and the projections (9, 10).

Moreover, according to a second example, see FIGS. 3A, 3B, called transmission-transmission, the following components are included:

- First resonator (1), configured as a ceramic disc for power applications, with a thickness of 2 mm and a diameter of 10 mm, and which has a main frequency of vibration in thickness of 1 MHz.
- Second resonator (2), made of ceramic for power applications, configured as a toroid with a rectangular cross section and a circular directrix, a thickness of 2 mm, with an external diameter of 20 mm, and an internal diameter of 14 mm, and which has a main frequency of radial vibration of 55 KHz.
- Transmission disc (14) with a diameter of 11 mm and variable thickness, arranged on the first resonator (1), in order to receive by transmission the vibration of the first resonator (1) and transmit said vibration from the first resonator (1) to the cavity (6).
- Cavity (6) with a variable height, about 3.5 mm, and a diameter of 11 mm, above the transmission disc (14).
- Head (3) for fastening the resonators (1, 2), and made up in part by the transmission disc (14), and which receives vibration by transmission from the first resonator (1).
- Housed portion (13) which makes up part of the head (3), and which is intended to be housed in the hole (7).

In the second example, a first radial mode of the second resonator (2) is used in order to stimulate a flextensional mode of the head (3), particularly of the housed portion (13), in low frequency, by radial transmission of the second resonator (2) to the walls of the head (3) to which it is adhered. The final frequency of the second resonator (2), together with the head (3), is a function of the overall flexion of the second resonator (2), in this case, 55 kHz. Also, the first resonator (1) operates by means of direct transmission by thickness mode of the HFS frequency.

In the second example, the vibrating membrane (8) is not incorporated, unlike the case of the first example, but rather a direct transmission of the waves from the resonators (1, 2) to the cavity (6) is encouraged. The first example incorporates the membrane (8) vibrating by flexion in order to obtain, jointly in the first resonator (1) and in the membrane (8), a resonance in LFS frequency, such as at 55 kHz, when the second resonator (2) emits in HFS, such as at 1-3 MHz. On the contrary, in the second example, for the first resonator (1), the emission and resonance frequencies of the first resonator (1) are similar, and are close to 1 MHz, such that there is only transmission instead of flexion. Hence, the model is called transmission-transmission, since there is transmission for the two frequencies, which are achieved directly. In both examples, the first and second frequencies have been interchanged: in the first example, the first frequency is LFS and the second frequency is HFS, while in the second example, it is the opposite.

For each of the two examples and, in general, for any embodiment of the invention, it is envisaged that the head (3) can be made of metal, for example aluminium, or alternatively a biocompatible material, such as a polymer, for example polypropylene.

The invention claimed is:

1. A wearable device for transdermal product supply, comprising:

a head, which includes:

a proximal area configured to be, when in use, closer to the skin of a user, a distal area, farther away from the skin of the user, and an outer cavity, defined in the proximal area, and configured to be oriented, when used, towards the skin of the user;

a first resonator, housed in the distal area of the head, for working in resonance at a first frequency, emitting ultrasound towards the skin of the user at the first frequency; and a second resonator, housed in the proximal area of the head, for working in resonance at a second frequency, emitting ultrasound in a direction parallel to the skin at the second frequency;

wherein one of the first and second frequencies is a high-frequency sonophoresis (HFS) frequency and the other frequency is a low-frequency sonophoresis (LFS) frequency, wherein the head is configured such that the head enables the waves emitted by the resonators to circulate through the head without encountering gaseous material before leaving the head; and wherein the second resonator comprises an inner through hole in order to enable the waves from the first resonator to pass through without hitting the second resonator, as well as a portion of the cavity of the head, corresponding to the height of the second resonator, is surrounded by the second resonator, and wherein the waves from the second resonator are directed through the head, the hole and the cavity, in order to bounce off the head in an opposite position and interfere with the waves from the first resonator.

2. The device according to claim 1, wherein the LFS frequency is in a range of 50-60 KHz.

3. The device according to claim 1, wherein the HFS frequency is in a range of 800-1200 KHz.

4. The device according to claim 1, wherein the first resonator has a disc shape.

5. The device according to claim 1, wherein the second resonator has a toroid shape.

6. The device according to claim 1, wherein the first resonator is intended to work in resonance at the LFS frequency, together with the head, and the second resonator at the HFS frequency.

7. The device according to claim 6, wherein the second resonator has a toroid shape with a fundamental frequency of vibration in thickness mode within the HFS range, in order to resonate in thickness mode at HFS frequency when supplied at HFS frequency, as well as the first resonator has a disc shape with a fundamental frequency of vibration in thickness mode within the HFS range, wherein the head additionally includes at least one component intended to be in contact with the first resonator, such that an assembly of the first resonator and head is formed, with physical continuity, which constitutes a transducer with a fundamental frequency in flextensional mode within the LFS range, in order to resonate at LFS frequency when it is supplied at LFS frequency.

8. The device according to claim 7, wherein the component comprises a membrane which is vibrating by flexion, and that is inserted between the first resonator and the second resonator, in contact with the first resonator.

9. The device according to claim 8, wherein the component additionally comprises two projections, one proximal and the other distal, between which the membrane is supported.

10. The device according to claim 1, wherein the first resonator is intended to work in resonance at HFS frequency and the second resonator at LFS frequency.

11. The device according to claim 10, wherein the first resonator has a disc shape, with a fundamental frequency in thickness mode within the HFS range, in order to resonate in thickness mode at HFS frequency when the first resonator is supplied with HFS frequency, as well as the second resonator has a toroid shape with a fundamental frequency, in radial mode, within the LFS range, in order to resonate, in radial mode, at LFS frequency when the resonator is supplied at LFS frequency.

12. The device according to claim 11, wherein the head additionally comprises a transmission disc, arranged on the first resonator, in order to communicate the vibration from the first resonator to the cavity by transmission.

13. The device according to claim 1, wherein the head is made up of one single monobloc body.

14. The device according to claim 1, wherein the head is made of a metal material or a biocompatible polymeric material.

15. The device according to claim 1, wherein the head comprises a housed portion which occupies at least a portion of the hole of the second resonator.

* * * * *